(12) United States Patent
Belleville

(10) Patent No.: US 11,369,277 B2
(45) Date of Patent: Jun. 28, 2022

(54) HYBRID IMAGE-INVASIVE-PRESSURE HEMODYNAMIC FUNCTION ASSESSMENT

(71) Applicant: OPSENS INC., Quebec (CA)

(72) Inventor: Claude Belleville, Ville de Quebec (CA)

(73) Assignee: Opsens Inc., Quebec (CA)

( * ) Notice: Subject to any disclaimer, the term of this patent is extended or adjusted under 35 U.S.C. 154(b) by 0 days.

(21) Appl. No.: 16/963,131

(22) PCT Filed: Jun. 27, 2019

(86) PCT No.: PCT/CA2019/050894
§ 371 (c)(1),
(2) Date: Jul. 17, 2020

(87) PCT Pub. No.: WO2020/000102
PCT Pub. Date: Jan. 2, 2020

(65) Prior Publication Data
US 2021/0244293 A1    Aug. 12, 2021

Related U.S. Application Data

(60) Provisional application No. 62/690,756, filed on Jun. 27, 2018.

(51) Int. Cl.
*A61B 5/0215* (2006.01)
*A61B 5/0275* (2006.01)
*A61B 5/00* (2006.01)

(52) U.S. Cl.
CPC .......... *A61B 5/0215* (2013.01); *A61B 5/0275* (2013.01); *A61B 5/6851* (2013.01)

(58) Field of Classification Search
CPC .......... A61B 5/02; A61B 5/0215; A61B 5/026; A61B 5/0275; A61B 5/489; A61B 5/72;
(Continued)

(56) References Cited

U.S. PATENT DOCUMENTS

| 5,048,534 A | 9/1991 | Marinus et al. |
| 5,150,292 A | 9/1992 | Hoffmann et al. |

(Continued)

FOREIGN PATENT DOCUMENTS

| EP | 3120762 | 1/2017 |
| WO | 2017055228 A1 | 4/2017 |

OTHER PUBLICATIONS

Nijjer et al. The Instantaneous wave-Free Ratio (iFR) pullback, Cardiovascular Revascularization Medicine, vol. 16, Issue 3, Apr.-May 2015, pp. 167-171. Available online Jan. 29, 2015 (Jan. 29, 2015).

(Continued)

*Primary Examiner* — Christian Jang
*Assistant Examiner* — Mitchell E Alter
(74) *Attorney, Agent, or Firm* — Benoit & Cote Inc.; Charles-Andre Caron

(57) ABSTRACT

There is described a method for calculating a patient-specific hemodynamic parameter. The method comprises measuring at least one pressure measurement in an artery using an intravascular pressure measurement device, and taking at least one medical image of the artery from a medical imaging instrument, the at least one medical image of the artery being synchronous with the at least one pressure measurement. Both the pressure measurement and the medical image are fed to a computing system to calculate a flow from the at least one medical image, to calculate parameters of the artery from at least two artery pressure drops and corresponding flow components, and based on the flow and the parameters of the artery, to calculate a patient-specific hemodynamic parameter or a plurality thereof.

15 Claims, 5 Drawing Sheets

(58) Field of Classification Search
CPC ...... A61B 5/6851; G16H 50/20; G16H 30/40; G16H 50/30
USPC .......................................................... 600/486
See application file for complete search history.

(56) References Cited

U.S. PATENT DOCUMENTS

| | | | |
|---|---|---|---|
| 2006/0052700 | A1 | 3/2006 | Svanerudh |
| 2014/0039276 | A1 | 2/2014 | Hattangadi et al. |
| 2014/0107935 | A1* | 4/2014 | Taylor ................. G06T 7/11 702/19 |
| 2015/0324962 | A1* | 11/2015 | Itu ..................... A61B 5/02007 382/130 |
| 2016/0350920 | A1 | 12/2016 | Kassab |
| 2017/0032097 | A1 | 2/2017 | Itu et al. |

OTHER PUBLICATIONS

Pyxaras et al. Co-registration of fractional flow reserve and optical coherence tomography with the use of a three-dimensional angiographic roadmap: an opportunity for optimisation of complex percutaneous coronary interventions, EuroIntervention 2013;9:889. Published: Nov. 2013 (Jan. 2013).

Bon-Kwon Koo, What Is the Clinical Relevance of the Discordance Between Fractional Flow Reserve and Coronary Flow Reserve? JACC, vol. 10, No. 10, 2017.

Aarnoudse et al. Direct volumetric Blood Flow Measurement in coronary arteries by thermodilution, JACC, vol. 50, No. 24, 2007.

Carrick et al. Comparative Prognostic Utility of Indexes of Microvascular Function Alone or in Combination n Patients With an Acute ST-Segment-Elevation Myocardial Infarction. Circulation 2016, 134:1833-1847.

Decchi et al. Coronary Microvascular Dysfunction and Prognosis in Hypertrophic Cardiomyopathy, N Engl J Med 2003; 349:1027-1035.

Jaffe et al. prevention and Treatment of Microvascular Obstruction-Related Myocardial Injury and Coronary N-reflow Following Percutaneous Coronary Intervention, JACC Cardiovasc Interv 2010; 3:695-704.

Morris et al. Fast Virtual Fractional Flow Reserve Based Upon Steady-State Computational Fluid Dynamics Analysis, JACC. vol. 2, No. 4, 2017.

Niccoli et al. Myocardial No. reflow in Humans, J Am Coll Cardiol 2009; 54:281-292.

Niida et al. Coronary physiological assessment combining fractional flow reserve and index of microcirculatory Yesistance in patients undergoing elective percutaneous coronary intervention with grey zone fractional flow reserve, Catheter Cardiovasc Interv. 2018;1-11.

Schwartz et al. Evaluation of Patients with chest pain and normal coronary angiograms, Catheter Cardiovasc Interv. 2018;1-11.

* cited by examiner

HYBRID IMAGE-INVASIVE-PRESSURE HEMODYNAMIC FUNCTION ASSESSMENT

CROSS-REFERENCE TO RELATED APPLICATIONS

This application claims benefit or priority of U.S. provisional patent application 62/690,756, filed Jun. 27, 2018, which is hereby incorporated herein by reference in its entirety.

BACKGROUND

(a) Field

The subject matter disclosed generally relates to a method for assessment of hemodynamic function. More specifically, it relates to a method for determining hemodynamic parameters using an intravascular pressure measurement device combined with medical imaging.

(b) Related Prior Art

Coronary artery diseases are currently diagnosed by assessing the impact of coronary stenosis on blood flow. A large number of clinical studies have shown the treatment of coronary stenosis based on the measurement of Fractional Flow Reserve (FFR) leads to the improvement of patient outcomes. FFR consists in taking the ratio of distal pressure (Pd) to proximal pressure (Pa). In the absence of coronary artery flow restricting lesion, FFR equals 1. As the blood flow restriction increases, the FFR value drops. The FFR ratio expresses the percentage of blood flow reserve in presence of the lesion compared to the same artery without any lesion. More specifically, it has been shown that deferring the treatment of a specific stenosis with an FFR value above 0.80, while treating the stenosis if the FFR value is equal or below 0.80, leads to an improved outcome for the patient.

Although FFR measures the severity of epicardial stenosis, the presence of microvascular dysfunction can increase the FFR value, underestimating the severity of a lesion. Coronary flow reserve (CFR) depends on both the epicardial and microvascular resistances. Therefore, discordance between FFR and CFR can occur in deciding whether a lesion should be treated or not. As both parameters are known to have prognostic values, the discordance between FFR and CFR illustrates the need for a refined diagnostic that would take the microvascular function into consideration [Bon-Kwon Koo, JACC, Vol. 10, No. 10, 2017]. Despite restoring normal epicardial flow in most cases of acute myocardial infarction, there remains a high rate of microvascular obstruction and myocardial necrosis [Niccoli G et al, J Am Coll Cardiol 2009; 54:281-292]. Elective coronary angioplasty is associated with up to 20% of periprocedural myocardial infarction, believed to be the result of micro-embolization [Jaffe R et al., JACC Cardiovasc Interv 2010; 3:695-704]. A significant proportion of patients with symptoms of stable angina present normal coronary arteries, for which the alteration in microvessel function is the factor contributing to the myocardial ischemia [Schwartz L et al., Arch Intern Med 2001; 161:1825-1833]. In patients with hypertrophic cardiomyopathy, microvascular dysfunction is a strong predictor of left ventricular dysfunction and death [Cecchi F et al, N Engl J Med 2003; 349:1027-1035]. Microvascular resistance was shown to be associated to left ventricular and clinical outcomes after ST-segment-elevation. Compared with standard clinical measures of the efficacy of myocardial reperfusion, including the ischemic time, ST-segment elevation, angiographic blush grade, and CFR, microvascular resistance was shown to have superior clinical value for risk stratification and may be considered a reference test for failed myocardial reperfusion [Carrick D. et al., Circulation 2016, 134:1833-1847]. Microvascular resistance, not FFR, is the strongest predictor of improvement of the coronary flow in grey-zone FFR lesions [Niida T. et al, Catheter Cardiovasc Interv. 2018; 1-11]

Although in recent years the understanding of coronary blood flow has mainly focused on the epicardial arteries, there is a growing body of evidence showing that microcirculation plays a key role in the diagnostic of ischemic patients which could ultimately lead to the most appropriate myocardial reperfusion treatment plan.

However, the measurement of microvascular resistance is not common practice in today's catheterization laboratory (or cath lab) as the methods are tricky and clinical workflow is disruptive. The microvascular resistance is typically calculated by dividing the distal pressure (Pd) by the flow within the artery. The distal pressure is commonly measured using a pressure sensitive guidewire. Various methods exist to measure blood flow. Doppler sensitive guidewire can be used to measure the velocity of blood. This method is sub-optimal due to poor wire handling characteristics and due to blood velocity measurement varying with the pointing direction of the wire portion comprising the Doppler sensor, which is operator-dependent and anatomy-dependent. Another method is based on the time it takes for the blood to reach the distal portion of the artery by measuring the time difference between the injection of a bolus of saline and its detection by a temperature sensitive guidewire located distally, also called thermodilution. Thermodilution method leads to variable transit time measurement, requiring multiple bolus of saline injection. It also assumes a constant artery volume between patients, hence also assuming minimal coronary disease. Recently, a new method is based on the measurement of blood mean temperature drop following continuous infusion of known flow rate of saline at room temperature [Aarnoudse W. et al., JACC, Vol. 50, N0. 24, 2007]. Although this last method is believed to be more accurate and reproducible, it requires the use of a special catheter and set-up that is likely to add to the procedure time and cost. Except for the Doppler based method, these methods measure the mean blood flow and therefore, they don't have the ability to measure time-dependent blood flow and time-dependent microvascular resistance (i.e., not applicable in cases in which the blood flow and the resistance are a function of time instead of being constant).

In recent years, there has been a lot of work in developing non-invasive image-based pressure-flow characteristics of coronary arteries in view of determining the Fractional Flow Reserve without the need for invasive pressure measurement. Patient-specific geometry of arteries measured using angiograms, CT-scan, MRI-scan, and other non-invasive imaging systems known in the art, are at the center of these non-invasive patient hemodynamic assessment. These methods involve building a closed-loop model that includes the contribution, among others, of the artery, the microvascular system and the heart. The heart and microvascular systems are modelled with lumped systems of resistance, inductance and capacitance, the heart also including a blood flow driving force. On the other hand, the arteries are usually modelled using well known Navier-Stokes equations, either using 3D computational models, reduced order computational model, multi-scale models that combine different types of models depending on specific feature of an artery segment. An artery can also be modelled using analytical or semi-analytical models or lumped model where the resistance, inductance and/or capacitance of the artery, or of a given segment of artery, are calculated using patient-specific geometry of the artery obtained from the non-invasive imaging system.

In order to resolve the closed-loop system and hence determine the pressure-flow characteristics of the artery, it is necessary to know the boundary and the initial conditions of the systems. Because these boundary and initial conditions are not known for the patient under evaluation, these models use generic parameters such as mean microvascular resistance, vessel elasticity, left ventricular contractility, all usually from the characteristics of general population. These assumptions may lead to significant errors in calculating the pressure-flow characteristics of an artery. Among all input parameters necessary to calculate the pressure-flow characteristics, the microvascular resistance amounts to 59% of all the errors [Morris et al., JACC. Vol. 2, No. 4, 2017]. Microvascular resistance variability among patient has indeed a direct impact on the accuracy of the pressure-flow characteristics as computed from the closed-loop model, as it was observed herein above with respect to clinical results. It is therefore not possible to determine patient specific microvascular resistance without the use of additional patient specific measurements.

U.S. patent application publication No. 2017/0032097, entitled "Method and system for enhancing image-based blood flow computations using physiological measurements" uses various measurements in order to calculate the microvascular resistance. A first method involves the measurement of the total time of flight ($T_{mn}$) for injected contrast agent to reach the distal portion of the artery, assumed to be equal to blood flow, and multiplying this $T_{mn}$ value by measured distal pressure (Pd) to get a microvascular resistance. This method assumes a generic mean artery volume that is not patient specific, therefore not considering patient disease in the artery. Also, it does not account for any time dependence of microvascular resistance. Other proposed methods are based on adding invasive pressure or flow measured values to various pressure-flow relations, such as 3D Computation Flow Dynamic (CFD), reduced order CFD, multiscale methods that combine different pressure-flow relations depending on the feature within the artery, analytical and semi-analytical methods, lumped model (resistance, inductance and capacitance model). Measured pressure or flow value is devoted to improve the accuracy of the model. However, these methods do not take full advantage of the presence of an invasive device within the coronary artery as they still rely to a significant extent on the pressure-flow/artery-geometry relations.

There is therefore a need for a system that reliably measures the microvascular resistance while being fast and easy to operate such that it is compatible with today's clinical workflow.

SUMMARY

According to an aspect of the invention, there is provided a method comprising:
  measuring at least one pressure measurement in an artery using an intravascular pressure measurement device;
  taking at least one medical image of the artery from a medical imaging instrument, the at least one medical image of the artery being synchronous with the at least one pressure measurement;
  feeding both the at least one pressure measurement and the at least one medical image to a computing system;
  calculating a flow from the at least one medical image;
  calculating parameters of the artery from at least two artery pressure drops and corresponding flow components; and
  based on the flow and the parameters of the artery, calculating a patient-specific hemodynamic parameter.

According to an embodiment, the steps of measuring the at least one pressure measurement and taking the at least one medical image are performed in two conditions of blood flow, wherein calculating parameters of the artery comprises solving a second-degree equation of the parameters of the artery using the at least two artery pressure drops and corresponding flow components which are measured in the two conditions of blood flow According to an embodiment, the two conditions of blood flow comprise a higher blood flow condition and a lower blood flow condition, the method further comprising administering an agent to cause higher blood flow condition prior to said steps of measuring the at least one pressure measurement and taking the at least one medical image under the higher blood flow condition.

According to an embodiment, the higher blood flow condition is induced by injection of contrast agent or hyperemic agent to induce partial or full hyperemia.

According to an embodiment, there is further provided the step of producing a sound signal when inducing the higher blood flow condition for timing the step of measuring the at least one pressure measurement with the injection of a microvascular dilator agent.

According to an embodiment, there is further provided the step of introducing a radiation-absorbing contrast medium in the artery, wherein taking the at least one medical image of the artery further comprises:
  measuring, in the at least one medical image, a diameter D of the artery which varies along a length x of the artery;
  tracking a propagation of the radiation-absorbing contrast medium in the artery and measuring a time taken for a propagation between a first point L1 to a second point L2 in the artery,
wherein calculating the flow comprises dividing a volume V, $$V = \frac{(L_2 - L_1)}{4} \cdot \int_{L1}^{L2} \pi (D(x))^2 dx,$$

by the time taken for the propagation to calculate a mean blood flow in the artery.

According to an embodiment, measuring, in the at least one medical image defining a plane, a diameter D of the artery which is perpendicular to the plane of the at least one medical image comprises using densitometry on the radiation-absorbing contrast medium to measure D as a function of x by applying Beer-Lambert's law on a measured intensity in a section of the artery.

According to an embodiment, there is further provided the step of inducing hyperemic condition using an intracoronary or intravenous injection of a hyperemic agent in the artery, and calculating the flow associated to the hyperemic condition using the parameters of the artery, wherein calculating the patient-specific hemodynamic parameter is based on a pressure drop and the calculated flow associated to the hyperemic condition.

According to an embodiment, the patient-specific hemodynamic parameter comprises a microvascular resistance.

According to an embodiment, the steps of measuring the at least one pressure measurement and taking the at least one medical image are performed in a resting condition, first during a systole period which covers at least a portion of a systole, and second during a diastole period which covers at least a portion of the diastole, wherein calculating parameters of the artery comprises solving a second-degree equation of the parameters of the artery using the at least two artery pressure drops and corresponding flow components which are respectively measured and calculated in the systole period and in the diastole period.

According to an embodiment, there is further provided the step of identifying a presence of a stenosis in the artery and identifying a segment distal from the stenosis which is free of any stenosis, and taking a plurality of pressure measurements along said segment.

According to an embodiment, identifying a presence of a stenosis comprises comparing one of the parameters of the artery with a predetermined threshold to identify a presence of a stenosis in the artery.

According to an embodiment, identifying a presence of a stenosis comprises using the at least one medical image to identify a presence of a stenosis in the artery by determining a presence of a luminal obstruction above 50%.

According to an embodiment, taking a plurality of pressure measurements along said segment is made by providing a tip of the intravascular pressure measurement device at a most distal location in said segment and pulling back the intravascular pressure measurement device.

According to an embodiment, there is further provided the step of calculating a geometry-based flow using the plurality of pressure measurements along said segment and numerically solving Navier-Stokes equations, and using the geometry-based flow to apply corrections to the parameters of the artery and to the step of calculating a flow from the at least one medical image, thereby applying a correction to the patient-specific hemodynamic parameter to account for the presence of the stenosis.

According to an embodiment, measuring the at least one pressure measurement and taking at least one medical image are synchronous by simultaneously acquiring the at least one pressure measurement and the at least one medical image in real time, or by time stamping the at least one pressure measurement and the at least one medical image.

According to another aspect of the invention, there is provided a system comprising:
 a computing system in communication with an intravascular pressure measurement device and with a medical imaging instrument, the computing system comprising a memory for storing instructions and data from both the intravascular pressure measurement device and the medical imaging instrument, and a processor which executes the instructions to:
 receive at least one pressure measurement from the intravascular pressure measurement device in an artery;
 receive at least one aortic pressure from another pressure device;
 receive at least one medical image of the artery from the medical imaging instrument;
 calculate a flow from the at least one medical image;
 calculate parameters of the artery from at least two artery pressure drops and corresponding flow components; and
 based on the flow and the parameters of the artery, calculate a patient-specific hemodynamic parameter.

According to an embodiment, the intravascular pressure measurement device is a pressure guidewire.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

The method according to an embodiment involves the simultaneous (or synchronous) combination of an invasive pressure measurement instruments, such as an intravascular pressure measurement device (e.g., a pressure guidewire) with a non-invasive instrument such as a medical imaging instrument which takes medical images of the artery. The method is for determining a blood flow with greater precision in order to determine other values which depends on a proper measurement of the blood flow.

Instead of using non-invasive instruments in replacement of invasive instruments, as typical in recent prior art methods, and which involves drawbacks as discussed above, the methods according to the invention use both together. This combination allows precise pressure measurements from the intravascular pressure measurement device and complement those with medical images that personalize the calculation of hemodynamic parameters with real data, in real time, on the geometry of the artery and flow data in the artery. The hemodynamic parameters are thus computed with a higher accuracy and better reflect the actual and real-time conditions in the artery than if no geometry or flow data were collected from the non-invasive instrument as proposed herein.

An object of the presently described embodiments is to provide clinical workflow compatible methods, i.e., fast and easy, that allow measuring or estimating the flow within a target artery, which along with intravascular pressure measurement allows calculating hemodynamic parameters such as microvascular resistance, coronary flow reserve (CFR) and Fractional flow reserve (FFR). It is also an object of the present embodiments to combine invasive pressure measurement to coronary artery images, in order to obtain accurate coronary flow, which when combined with intravascular pressure measurements, allows the calculation of hemodynamic parameters.

Figure 1:
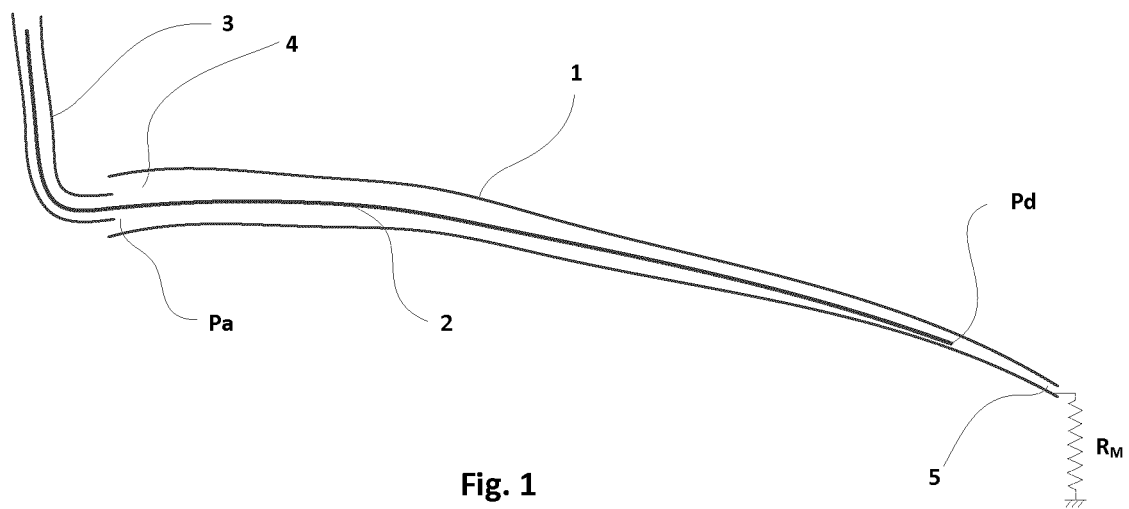
FIG. 1 is a schematic cross-section view illustrating an intravascular pressure measurement device taking a pressure measurement in an artery, according to an embodiment.

FIG. 1 illustrates a typical set-up used to assess the hemodynamic function of a patient with coronary artery disease (CAD). Epicardial artery 1 directs blood flow from the ostium 4 of the artery to the distal end 5, where blood enters the microvascular system where oxygen exchange occurs. The microvascular resistance is illustrated herein by a single resistance $R_M$. It will be shown later that it is also possible to model the microvascular system to take into consideration other physiologic functions such as the myocardium capacitance. In a typical set-up, a guiding catheter 3 is placed at the ostium of the artery. The guiding catheter can be used to deliver contrast agent used to reveal the contour of the artery; to guide medical devices such as pressure guidewire 2 to the ostium of the artery and further distal in the coronary artery; to measure blood pressure at the entry of the artery, herein called the aortic pressure Pa. The aortic pressure can be used as a boundary condition forcing the blood to flow within the artery. Distal pressure Pd measured by the pressure guidewire can also be used as a boundary condition.

Figure 2:
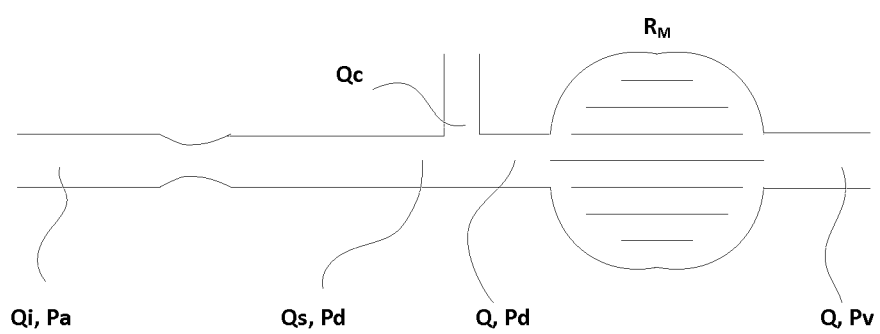
FIG. 2 is a schematic cross-section view illustrating a modelized artery, according to an embodiment.

FIG. 2 illustrates a functional equivalent of the vascular system. The blood flow and pressure at the ostium (i.e., proximal pressure) can be represented by Q and Pa, respectively. The epicardial may contain a stenosis that creates a pressure drop Δp, leading to distal pressure Pd at the distal end of the artery. Flow Q is conserved if one assumes there is no significant branch between the ostium and the distal end. Collateral vessels (aka collaterals) may also be present in certain patients. When present, a collateral usually connects to the main vessel at a distal location relative to the pressure guidewire measuring point Pd, hence between the Pd point and the microcirculation system. The collateral contributes additional blood flow to the microcirculation, hence reducing both the flow and the pressure drop across the stenosis. Although the flow from the collateral adds to the epicardial flow, distal pressure before and after the collateral does not change, this allows taking into consideration the contribution of collaterals flow in FFR measurement. FFR is defined by relation 1, where $Q^N$ is the flow in the absence of stenosis (normal artery), and $Q^S$ is the flow in presence of the stenosis, both flows obtained under stress condition, i.e., under full hyperemic condition (normally induced by a hyperemic agent such as adenosine). It is reasonable to assume that the flow is a linear function of the pressure, the microvascular resistance $R_M$ being the proportional parameter between these quantities, where flow can be expressed in terms of microvascular pressure difference and associated resistance $R_M$. Considering the microvascular resistance $R_M$ is minimal and does not change whether there is a stenosis or not and considering the venous pressure (Pv) is negligible (Pv≈0), FFR is obtained from the last part of relation 1.

$$FFR = \frac{Q^N}{Q^S} = \frac{(P_d - P_v)/R_M}{(P_a - P_v)/R_M} \approx \frac{P_d}{P_a} \qquad 1$$

Distal pressure measurements obtained from a pressure guidewire can be associated to the distal position of the artery by co-registering the pressure with position on the image. Co-registering means simultaneously measuring and recording both values. It is also possible to take more than one pressure measurement along the artery and co-registering more than one pressure and associated positions on the image. It is furthermore possible to pull-back the pressure guidewire 2 while recording the images and co-registering the measured pressure along the artery with positions on the images that are associated to each of the pressure measurements. A given pressure measurement can be localised in the artery by detecting the edge of the tip of the pressure guidewire 2, where the pressure sensor is located and where the radio-opacity abruptly changes because of the radio-opaque tip presumably provided on the tip of the pressure guidewire 2.

Prior art systems devoted to combine invasive measurement with image to either improve accuracy or ease the calculation of a hemodynamic function are strongly dependent on the geometry of the acquired images, by computing the pressure-flow characteristics of the artery from 3-D computational flow dynamic (CFD), reduced order CFD, 0-D analytical models or other lumped models. All these models are based on the geometry of the artery to model the pressure-flow characteristics. It is therefore a purpose of the present embodiments to develop pressure-flow characteristics less sensitive to the geometry of the artery to improve the eventual assessment performed by the measurement instruments (pressure guidewire 2 and imaging instruments).

It is understood the embodiments below comprise at least one computer used to acquire, store, process, displays, transmits or otherwise indicated herein below to use and measured data. A computer is understood to be any system that comprises a processing unit, a memory and required ports of communication to able to perform logical operations on signals.

Mean Blood Flow Measurement

A first embodiment is proposed below to measure artery-specific hemodynamic parameters without the need for a 3-dimensional image re-construction and with minimal dependence on the local geometry of the artery. A radiation absorbing contrast medium is introduced at the ostium of the artery. It is possible to track the propagation of the contrast agent and therefore, determine the time it takes for the blood to propagate from one point to another.

Various prior art methods exist to track this propagation of the contrast agent, including methods described in U.S. Pat. No. 5,150,292 entitled "Method and system for determination of instantaneous and average blood flow rates from digital angiograms" and in U.S. Pat. No. 5,048,534 entitled "Method of and device for determining quantities characterizing the flow of a liquid in a vascular system", both incorporated herein by reference. US patent application US 2017/0032097, also incorporated herein by reference, uses a similar method to measure the time it takes for the blood to reach the distal position of the artery. The flow in that prior art document is then calculated using the same relation as the one used for measuring the flow by thermodilution, which takes the inverse of the time to reach the distal end of the artery ($Q \sim 1/T_{mn}$). It assumes the volume of the specific targeted artery is the same as the mean artery volume of a general population, so it is neither patient-specific nor artery-specific. Because thermodilution methods that use temperature sensitive guidewire are not image-based systems, they do not have easy access to the specific volume of the patient artery under investigation.

A method according to an embodiment of the invention rather involves combining the volume of the targeted artery to the calculation of the flow and hence, to the calculation of hemodynamic parameters. The volume of the artery can be obtained by resolving relation 2, below. $L_1$ is the initial position where the contrast agent tracking starts, typically at the ostium of the artery, and $L_2$ is the position where the pressure sensitive portion of the pressure guidewire is located. $D(x)$ is the diameter of the artery measured by detecting the contour of the artery using well known edge detection methods. The diameter is integrated along the length of the artery, i.e., along the centerline of the artery.

Volume flow $Q_{mn}$ is calculated by dividing the volume of the artery V, by the time for the contrast agent to travel from $L_1$ to $L_2$. Hemodynamic parameters such as microvascular resistance $R_M$ is calculated by dividing the invasive distal pressure measurement Pd by volume flow $Q_{mn}$. Coronary flow reserve (CFR) can also be calculated by dividing the blood flow measured in hyperemia by the blood flow measured at rest (i.e., not in hyperemia).

$$V = \frac{(L_2 - L_1)}{4} \cdot \int_{L1}^{L2} \pi(D(x))^2 dx \quad 2$$

$$Q_{mn} = V / T_{mn} \quad 3$$

$$R_M = \frac{P_d}{Q_{mn}} \quad 4$$

Relation 2 assumes the artery is circular, while it is never the case for diseased arteries where the lumen can be substantially non-circular. Depending on the view, non-circularity can lead to either the over-estimation or under-estimation of the section of the artery. The impact on the calculated total artery volume is quite minimized by the fact that over and under estimation counter-balances over the length of the artery. As opposed to any of the geometry based CFD derived pressure-flow characteristics which are very sensitive to local specific geometry, this method is based on the overall geometry and is therefore much less sensitive to local geometry inaccuracies.

Notwithstanding the relative insensitivity of this method to local non-circular artery geometry, it is possible to improve lumen area accuracy by using the density of the contrast agent, i.e., using densitometry methods. It is known by those skilled in the art that the absorption of radiation by a contrast agent depends on the depth of absorbing medium the radiation travels through (Beer-Lambert's law). It is therefore possible to estimate the perpendicular component of the artery by measuring the absorption that occurs in the section area.

The level of radiation transmitted through an absorbing medium is expressed according to relation 5, where $I_i$ is the incident radiation intensity, $I_T$ is the transmitted radiation intensity, th is the thickness of absorbing medium, i.e., the depth of artery perpendicular to the plane of view, and $\alpha$ is a constant that corresponds to the contrast agent absorbing coefficient. It is possible to estimate $\alpha$ by measuring the $I_{T-cal}$ in a section of the same artery, or of another artery, where it is known to be circular, for example where it is assumed without disease. Similarly, one can also use the guiding catheter for the purpose of getting $\alpha$. $I_{i-cal}$ is obtained by taking a value nearby the position of $I_{T-cal}$, but outside the artery section, while $th_{cal}$ is the diameter of the artery in the plane of image. $\alpha$ is calculated using relation 6. Knowing $\alpha$, it is possible to estimate the diameter of the artery using relation 7, where $I_T$ is the intensity of the section of artery for which the perpendicular diameter is sought, $I_i$ is the intensity nearby this section, but outside the artery. Instead of taking the intensity $I_i$ nearby the artery, it is also possible to take any point in the background outside of the artery by first applying the digital subtraction angiography (DSA) method, which consists in removing background features by subtracting images absent of contrast agent from images with contrast agent. Considering relations 5 to 7, logarithm of pixel intensities must be subtracted.

$$I_T = I_i \cdot e^{-\alpha \cdot th} \quad 5$$

$$\alpha = -\frac{\ln I_{T cal} / I_{i cal}]}{th_{cal}} \quad 6$$

$$th = -\frac{\ln\left[\frac{I_T}{I_i}\right]}{\alpha} = \frac{\ln\left[\frac{I_i}{I_T}\right]}{\alpha} = \frac{\ln(I_i) - \ln(I_T)}{\alpha} \quad 7$$

Diastolic Flow Measurement

Second order polynomial can be used to model the pressure-flow relation of a given artery, the first order term relating to the viscous friction loss and the second term relating to the flow separation. In the prior art, the polynomial terms are found by analyzing the geometry of the artery, segmenting the artery to apply geometry-based analytical models adapted to each one of the artery segments. It is therefore quite sensitive to the exact artery geometry, especially when modelling a stenosis, where a complex stenosis is modeled as an idealized stenosis, notably with smooth variation and symmetrical progression of the section area. However, such geometries are never observed in a real context, which makes these prior art methods prone to produce an error in the result.

Therefore, another embodiment of the invention is based on the calculation of a second order polynomial characterizing the artery that is not related to the artery geometry, but which, instead, is related to its functional characteristics.

Figure 3:
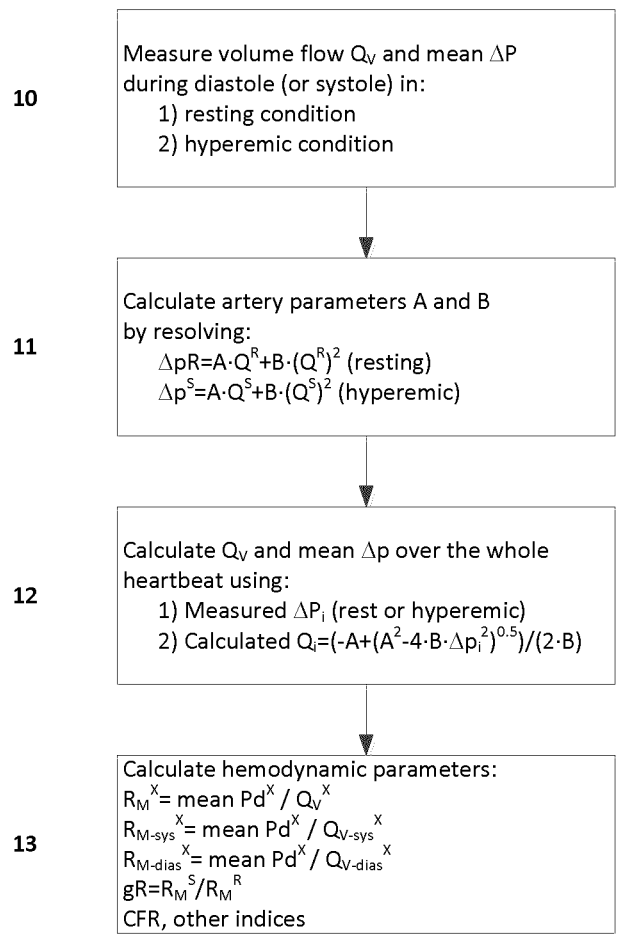
FIG. 3 is a flowchart illustrating a method for determining hemodynamic parameters with diastolic flow measurements and with a hyperemic agent, according to an embodiment.

An embodiment of the method is illustrated in FIG. 3 and described hereinbelow, assuming a synchronicity between the images and pressure measurements, either by simultaneously acquiring both modalities in real time or by time stamping both acquisitions. Considering the time $T_{mn}$ it takes for the contrast agent to reach the distal end of the artery is typically shorter than one heartbeat cycle, this method leads to accurate flow measurement if the flow within a heartbeat cycle is constant. The flow during the diastolic phase is however much higher than during the systolic phase, except for a few exceptions where the systolic flow is higher than diastolic flow in the right coronary artery (RCA) of certain patients. In step 10, since the flow mostly propagates during the diastole, where the flow is, to some extent, constant, the flow is measured as indicated in previous embodiment, but limiting volume flow measurement to the diastolic period, or to a portion of the diastolic period. It is understood here that although it is preferable measuring flow during the diastole as it is higher, the same can also be performed during the systole, or during a portion of the systole. With the patient at rest, the diastolic volume flow $Q^R$ is measured along with the pressure drop $\Delta p_i^R = (P_a - P_{di})^R$, where i is an index corresponding to a sequence of pressure measurements at a given rate, typically around 125 Hz. While inducing hyperemia to the patient (stressed patient) using a hyperemic agent (such as adenosine) or more generally a microvascular dilator agent, volume flow $Q^S$ and pressure drop $\Delta p_i^S$ are measured again during diastolic period while the patient is in hyperemia. The use of a microvascular dilator agent allows, first, taking measurements in a first blood flow condition, and then taking measurements in a second blood flow condition, typically involving microvascular dilation induced by a proper agent, thus resulting in a higher blood flow in the second blood flow than in the first blood flow condition (which has normal flow, or lower flow when compared to the second blood flow condition).

Using above measured values in step 11, it is possible to calculate parameters A and B (FIG. 3, step 10) characterizing the artery by resolving relations 8 and 9 for A and B.

$$\Delta p^R = A \cdot Q^R + B \cdot (Q^R)^2 \text{(at rest)} \qquad 8$$

$$\Delta p^S = A \cdot Q^S + B \cdot (Q^S)^2 \text{(stressed)} \qquad 9$$

where, $$\Delta p^X = \Sigma_{n_1}^{n_2} \Delta p_i^X / (n_2 - n_1)' \qquad 10$$

and where X above designates either R (Rest) or S (stressed), and $n_2$ and $n_1$ are boundaries of the period (diastole or portion of diastole) over which the flow was measured.

Knowing the artery parameters A and B, it is now possible in step 12 to calculate instant flow associated with any pressure drop (Pa–Pd). The next step is to calculate, using relation 11, flow $Q_i^X$ for each pressure drop measurements $\Delta p_i = Pa_i - Pd_i$ over the whole heartbeat cycle with the patient either at rest or in hyperemia. Volume flow can finally be calculated over a period of interest n2, n1 using relation 12, n2 and n1 being selected to obtain values over the whole heartbeat, during diastole or systole only, or other time frames.

$$Q_i^X = \frac{\left(-A + \sqrt[2]{A^2 - 4 \cdot B \Delta p_i^2}\right)}{2 \cdot B} \qquad 11$$

$$Q^X = \sum_{n_1}^{n_2} Q_i^X / (n_2 - n_1) \qquad 12$$

Microvascular resistance $R_M$ is then calculated in step 13 over the portion of the heartbeat of interest such as whole heartbeat, systole or diastole, either at rest or in hyperemia, using relation 13, where $P_d^X$ is the mean distal pressure over the same period of interest as the period used to calculate $Q^X$ (relation 14). It is also possible to calculate any combination of microvascular resistance, such as the ratio between hyperemic and a resting resistance. It is also possible to calculate other indices such as CFR using relation 15 among others.

$$R_M^X = \frac{P_d^X}{Q^X} \qquad 13$$

$$P_d^X = \sum_{n_1}^{n_2} P_{d_i}^X / (n_2 - n_1) \qquad 14$$

$$CFR = \frac{\sum_{n_1}^{n_2} Q_i^S}{\sum_{n_1}^{n_2} Q_i^R}, \qquad 15$$

where $n_2$ and $n_1$ selected to cover the whole heartbeat cycle. Other boundary limits can also be selected to calculate a ratio of hyperemic to resting flow (i.e., a ratio between measurements made in a first blood flow condition and in a second blood flow condition, involving a higher flow than in the first condition as a consequence of the microvascular dilator agent).

Contrast Induced Hyperemia Flow Measurement

Continuous hyperemia can be induced by various methods, most commonly using constant intravenous infusion of adenosine. Intravenous adenosine or other continuous infusion of hyperemic drug is however not available in every catheterization laboratory, or "cath lab". It is also possible to induce transient hyperemia with intra-coronary (IC) bolus of adenosine or other drugs. Because the duration of IC induced hyperemia is quite short, the operator would have to synchronize the injection of the hyperemic drug with the injection of the contrast agent, a method that may be challenging. Another embodiment consists in injecting a contrast agent once to measure the flow at resting condition (or first blood flow condition) as described in embodiments above, followed shortly after by a second injection of contrast, somewhat synchronized with hyperemia (or second blood flow condition) induced by contrast agent, which acts as a microvascular dilator agent that increases the blood flow to change the blood flow condition from normal to high. Contrast agent is indeed known to induce hyperemia up to nearly 80% of full hyperemia. The second flow measurement does not need to be taken while in full hyperemia, as long as the second order term of artery parameter B develops, and the pressure measurement is synchronized with contrast agent-based flow measurement, artery parameters A and B will be measured with adequate accuracy. Flow can then be calculated for resting condition and hyperemic condition by using measured $\Delta p^S$ and $\Delta p^R$ respectively.

As further described below, flow and pressure differences can be measured over the whole heartbeat cycle or over the diastole or systole only. Microvascular resistance and other hemodynamic parameters are calculated as described in previous embodiment using flow and pressure, either using the entire heartbeat or portion of it such as the diastole or systole.

Systolic/Diastolic Flow Measurement

Figure 4:
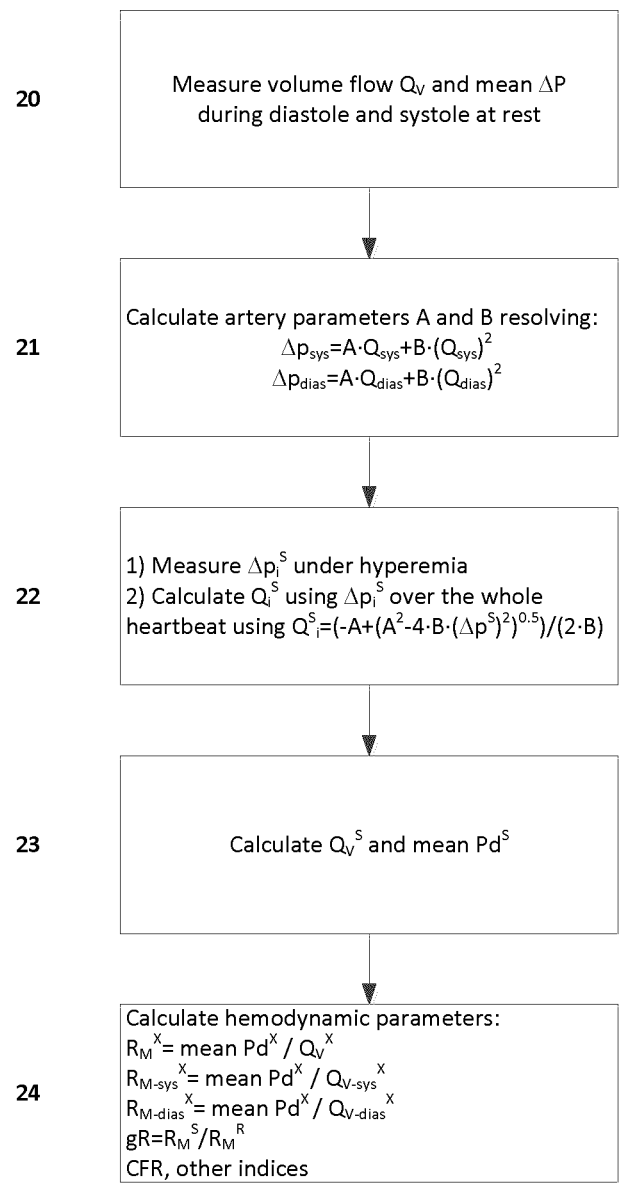
FIG. 4 is a flowchart illustrating a method for determining hemodynamic parameters with systolic and diastolic flow measurements and without any hyperemic agent, according to an embodiment.

Another preferred embodiment illustrated in FIG. 4 has the advantage of not requiring any hyperemic agent. In step 20, volume flow and mean pressure difference (Pa–Pd) are measured as described with respect to previous embodiments by tracking the contrast agent wave front during certain periods of the heartbeat cycle, along with determining the volume of the artery under investigation. Considering the blood flow is quite different during systole and diastole, the volume flow will be measured separately during systole $Q_{sys}$ and diastole $Q_{dias}$. Both these periods (systolic vs. diastolic) act as first and second blood flow conditions, in a way which is analogous to resting vs. hyperemic conditions. More than one injection of contrast may be required to cover both the systolic and diastolic periods. An audio signal may also be used to help the operator inject the contrast agent at the proper time.

From resting volume flows $Q_{sys}$ and $Q_{dias}$, and resting mean pressure differences $\Delta p_{sys}$ and $\Delta p_{dias}$, artery parameters A and B are calculated in step 21 as described in previous embodiment.

Measurement of a pressure difference during a single heartbeat does not require continuous hyperemia and therefore pressure difference $\Delta p_i^S$ is easily measured following the injection of an intracoronary bolus of adenosine or the like. As illustrated in step 22, $\Delta p_i^S$ then used to calculate instant flow $Q_i^S$ using relation 11, where A and B were found in step 21.

Volume flow $Q_v^S$ (or $Q_v^R$) and distal pressure $Pd^S$ (or $Pd^R$) are calculated for the period of interest using relations 12 and 14.

Microvascular resistance and other hemodynamic parameters are calculated in step 24 as described in previous embodiments.

Geometry-Based Model Flow Measurement Enhancement

Although the use of contrast agent front wave tracking methods described above to measure flow in an artery delivers adequate accuracy for the purposes herein, there may be cases where there is a need to further improve the result. 1-D CFD model cannot be used in artery comprising a stenosis as the abrupt changes of cross sectional areas cause the flow to develop velocity components perpendicular to the propagation axis along the artery, components that are not taken into consideration by a 1-D CFD model. 0-D pressure drop models can also be used, but pressure-drop stenosis models as mentioned previously assume ideal stenosis geometries that never exist in clinical set-ups.

Figure 5:
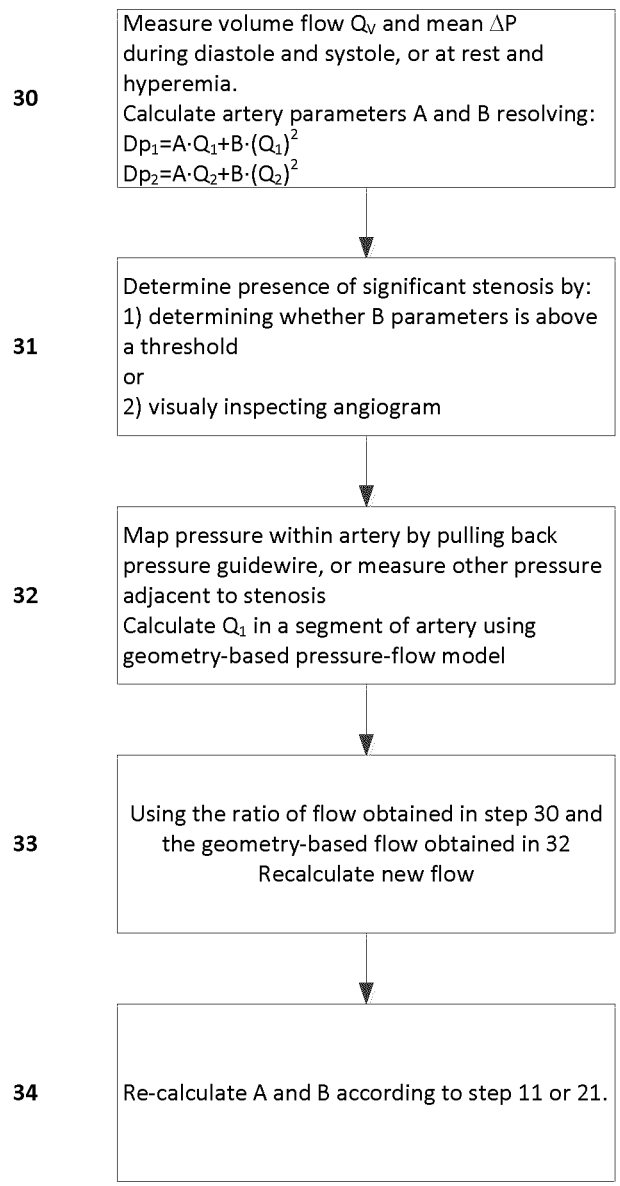
FIG. 5 is a flowchart illustrating a method for determining hemodynamic parameters with systolic and diastolic flow measurements and without any hyperemic agent, with geometric correction, according to an embodiment.

Another embodiment of the invention illustrated in FIG. 5, starts with the measurement of pressure and flow using contrast agent as described above and represented by step 30 in this embodiment, followed by the calculation of the artery parameters as before. In step 31, the presence of a significant stenosis is identified either by way of artery parameter B being above a predetermined threshold, or by way of visually identifying on the angiogram the presence of a local stenosis with a percentage luminal obstruction above 50%, above 60%, above 70% or above another pre-determined threshold percentage of obstruction.

In step 32, additional pressures are measured along the artery segment by slowly pulling back the pressure guidewire while co-registering pressure along with associated images associated to each of the pressure measurements along the segment, as described above. Alternatively, multiple (two or more) pressure measurements can be recorded at known positions within the artery; minimally the pressure is measured at a location distal to the stenosis if the stenosis is proximal in the artery under investigation, or proximal to the stenosis if the stenosis is distal, or pressures otherwise adjacent the stenosis and preferably in the longest segment of artery not containing stenosis. Let us assume herein below that the stenosis is located in the proximal portion of the artery.

The flow in the segment of artery for which other pressure is measured in step 32 can be calculated using well known 1-D CFD models because it does not contain stenosis. 1-D CFD model can be derived from Navier-Stokes equations which lead to resolving relations 16 and 17.

$$\frac{\partial A}{\partial t} + \frac{\partial Q}{\partial z} = 0 \quad\quad 16$$

-continued $$\frac{\partial Q}{\partial t} + \frac{\partial}{\partial z}\left(\alpha \frac{Q^2}{A}\right) + \frac{A}{\rho}\frac{\partial p}{\partial z} + K_R \frac{Q}{A} = 0, \quad\quad 17$$

where $\rho$ is the density of blood, $\alpha$ is the Coriolis coefficient and $K_R$ is a resistance related to blood viscosity and velocity profile. If we assume the artery is not elastic and considering there are no bifurcation, both terms of relation 16 equals to 0 a stated above.

An alternative to the use of CFD models to calculate the flow in the artery segment is to use other geometry-based models such as Poiseuille pressure-drop models, a lumped model, or other equivalently appropriate models. Poiseuille's law is expressed in relation 18. Flow Q can thereafter be calculated using the first part of relation 19 in situation where the pressure guidewire is slowly pulled back while taking pressure measurements and the pressure is thereby mapped along the axis of the artery; otherwise the last part of relation of 19 is used.

$$\Delta p = \frac{8\nu l}{\pi d^4} Q \quad\quad 18$$

$$Q_{geom} = \sum_i \Delta p_i \Big/ \frac{8\nu}{\pi} \cdot \sum_i \frac{l_i}{d_i^4} = \Delta p \Big/ \frac{8\nu}{\pi} \cdot \sum_i \frac{l_i}{d_i^4}, \quad\quad 19$$

where $\nu$ is the viscosity of blood, l is the artery length and d is the diameter of the artery. It is understood that $Q_{geom}$ can be any of the whole heartbeat mean flow, mean systolic or diastolic flow, either calculated for the resting condition or the hyperemic condition. It will depend on the portion of $\Delta p_i$ that is used, and on whether pressure was acquired at rest or at hyperemia.

Let us assume $Q_{geom}^R$ is the mean flow at rest. Although the measurement of volume flow using contrast agent method may contain some bias errors in determining the absolute volume flow, the ratio of two flows as obtained in step 30 certainly delivers a more accurate result as the impact of bias errors is reduced. It is therefore possible to re-calculate in step 33 the hyperemic flow $Q_{geom}^S$ by assuming the ratio of previously measured flow is accurate and therefore, corrected flow is obtained with relation 20.

$$Q_{geom}^S = Q_{geom}^R \cdot \frac{Q^S}{Q^R} \quad\quad 20$$

Geometry-based flow $Q_{geom}^R$ and $Q_{geom}^S$ and the associated pressure drop are used to re-calculate (step 34) new artery parameters A and B according to one of the steps 11 or 21. Artery-specific hemodynamic parameters can be calculated as previously described.

Segmentation of Artery

Figure 6:
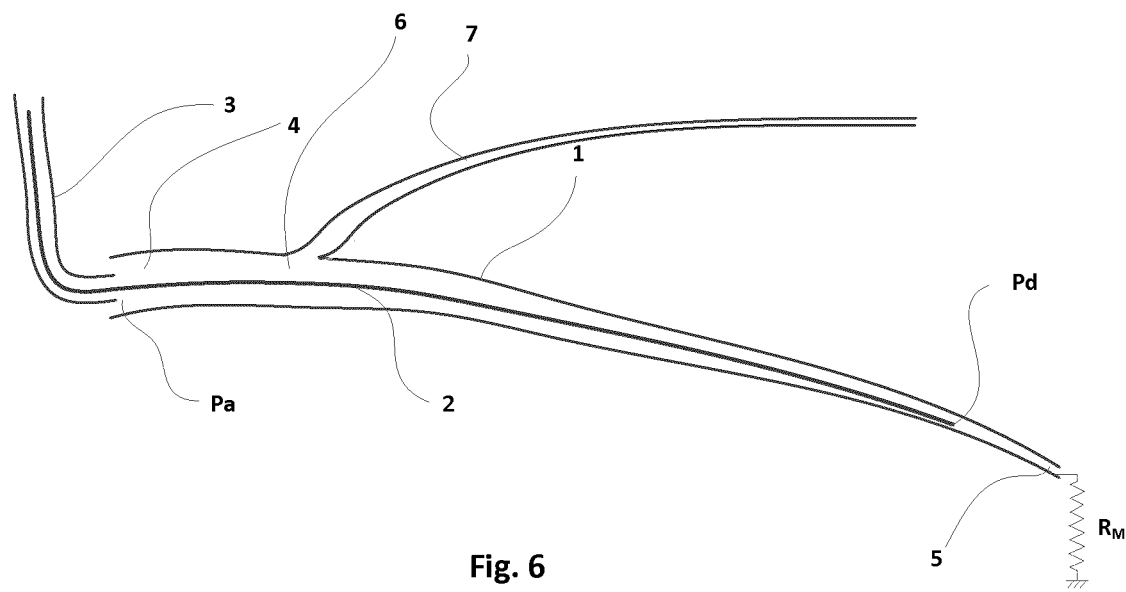
FIG. 6 is a schematic cross-section view illustrating an intravascular pressure measurement device taking a pressure measurement in an artery having a branch, according to an embodiment.

A significant branch 7 as shown in FIG. 6 may lead to the over estimation of the flow since the volume proximal to the branch carries blood flow that is diverted to the branch and hence, the volume of the artery in relation 3 should be reduced proportionately. One method of determining the ratio of flow splitting is to use well known the allometric scale law such as described in U.S. patent application publication 2016/0350920 entitled "Methods for the determination of transit time circulatory systems and applications of the same", incorporated herein by reference. It is otherwise possible to determine the splitting ratio by measuring the flow in the branch and the artery using contrast agent front wave tracking methods. The volume proximal to the branch used in calculating the flow in relation 3 is corrected by multiplying the proximal volume by the ratio $Q_{artery}/Q_{branch}$.

The method above would lead to reasonably accurate results if there is no significant pressure drop in the portion of the artery proximal to the branch. In case there is a significant stenosis, one method consists in measuring the pressure in the bifurcation 6, i.e., distal to the stenosis, and measure the flow-pressure relation in the segment of the artery distal to the stenosis. Another method consists in taking the two segments separately and calculate two sets of artery parameters A and B and calculating respective flows, hence microvascular resistance and other hemodynamic parameters.

By pulling back the pressure guidewire 2 in the artery while taking pressure measurements along the path of the pulling-back movement, it is possible to separate the artery into a series of segments, and calculate the artery characteristics A and B, hence calculate the hemodynamic parameters of interest.

Microvascular Resistance with Collateral

Collaterals are epicardial vessels connecting arteries together. As illustrated in FIG. 2, collaterals connection is most typically distal to the reach of pressure guidewire 2 when it extends fully distally. At rest, collaterals typically remain closed. In hyperemia (e.g., when a hyperemic agent is given to the patient), the presence of a stenosis makes the pressure at the distal end drop significantly, creating a pressure differential with the pressure of the supplying artery, hence opening the collateral. Collateral increases the flow through the microcirculation, while it contributes also increasing distal pressure Pd. This contribution to flow and pressure is not linear and therefore, it does not counterbalance.

A method to minimize the error caused by the unknown supply of blood flow from a collateral consists in isolating the contribution of the collateral by measuring the wedge pressure and include it in the calculation of the microvascular resistance (Martinez et al, Cor. Art. Dis., 2015). Because wedge pressure is not part of everyday clinical workflow, another method was developed that uses a relation between the $FFR_{myo}$ and $FFR_{cor}$ derived from general population. There is a need to better take into account the contribution of collaterals in the measurement of the microvascular resistance.

The systolic and diastolic hyperemic microvascular resistances in presence of a collateral can be expressed with relations 21.

$$R^S_{M-sys} = \frac{P^S_{d-sys}}{(Q^S_{A-sys} + Q^S_{C-sys})} \text{ and } R^S_{M-dias} = \frac{P^S_{d-dias}}{(Q^S_{A-dias} + Q^S_{C-dias})} \quad 21$$

where $Q_A$ is the flow from the artery under investigation and Qc is the collateral flow.

As discussed, a collateral opens in response to hyperemia and therefore, resting microvascular resistances can be expressed with relations 22.

$$R^R_{M-sys} = \frac{P^R_{d-sys}}{Q^R_{A-sys}} \text{ and } R^R_{M-dias} = \frac{P^R_{d-dias}}{Q^R_{A-dias}} \quad 22$$

If we assume the pressure driving the blood flow through the collateral is Pa, collateral flow can be expressed as follow:

$$Q^S_{C-sys/dias} = \frac{\Delta p^S_{d-sys/dias}}{R_C} \quad 23$$

where Rc is the resistance of the collateral and $\Delta p^S_{d-sys/dias}$ is either the systolic or diastolic hyperemic pressure difference Pa–Pd. Collateral resistance is not flow-dependent and therefore, $R_{C-sys} = R_{C-dias} = R_C$.

The ratio K of the diastolic to systolic resistance at rest can be calculated from relations 22 as follow.

$$K = \frac{R^R_{M-sys}}{R^R_{M-dias}} = \frac{Q^R_{dias}}{Q^R_{sys}} \cdot \frac{P^R_{d-sys}}{P^R_{d-dias}} \quad 24$$

Assuming the ratio of systolic to diastolic resistance in hyperemia is the same as the ratio at rest, relations 21, 23 and 24 leads to:

$$R_C = \frac{(K \cdot P^S_{dias} \cdot \Delta P^S_{d-sys} + P^S_{sys} \cdot \Delta P^S_{d-dias})}{(P^S_{dias} \cdot \Delta P^S_{d-dias} + P^S_{dias} \cdot \Delta P^S_{d-sys})} \quad 25$$

Collateral flow $Q_C^S$ can be calculated using Rc of relation 25 into relation 23. Hemodynamic parameters can then be calculated by considering the flow within the microvascular resistance is the addition of $Q_C^S$ and $Q_A^S$ Post-PCI Hemodynamic Assessment In resting condition, the relation between pressure and flow is typically linear. In presence of two or more stenoses, it is possible to easily determine the impact of stenting one stenosis (after performing a percutaneous coronary intervention or PCI) by removing the pressure drop caused by the stenosis to be removed, and calculate the distal pressure and the post-PCI value of any of the existing resting indices such as Pd/Pa, iFR (instantaneous Wave-free index) or dPR (diastolic pressure ratio). This is however not possible for FFR as it is a hyperemic index. A method to determine the impact on FFR after removing one stenosis requires wedge pressure measurement. As mentioned previously, this is not common practice in clinical set-ups.

Figure 7:
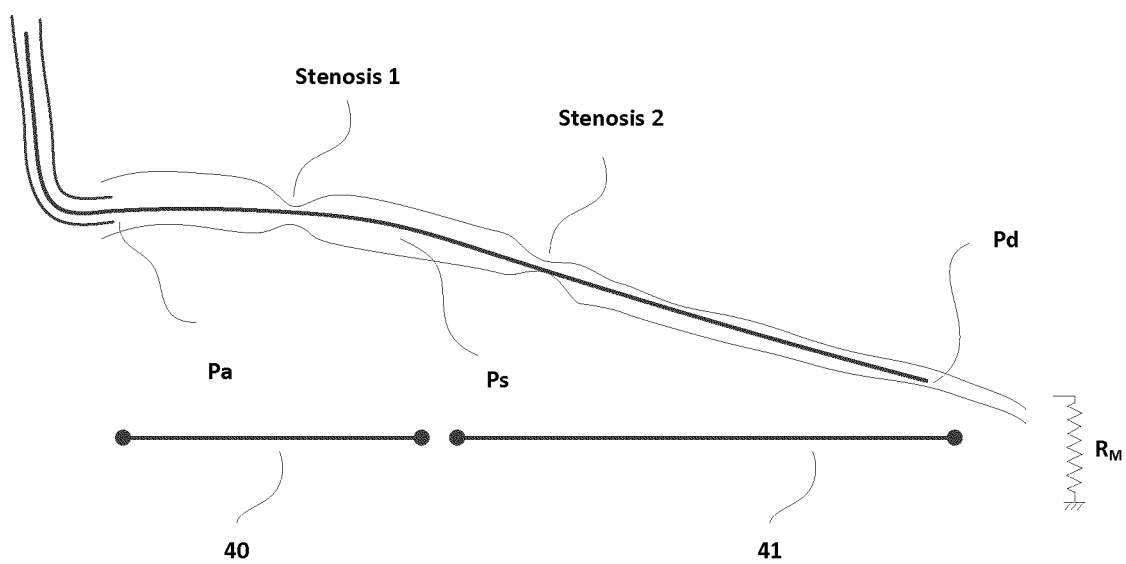
FIG. 7 is a schematic cross-section view illustrating an intravascular pressure measurement device taking a pressure measurement in an artery, with segmentation shown to isolate different stenoses in different segments, according to an embodiment.

A preferred way would involve characterizing the artery according to one of the previous methods, preferably a method that includes segmenting the artery. Although segmentation may include the two stenoses and along with other portions of the artery, for the sake of simplifying the description, we will herein assume the segments include a first segment 40 from the ostium to the middle of the stenoses and a second segment 41 from the middle of the artery to the distal end (FIG. 7). This obviously assumes there is no significant diffuse disease. As already mentioned, if the lesions are diffuse along the artery, they can be modeled by additional segmentations. Let us assume flow is measured according to step 10 or 20, and pressure is measured according to step at both the distal end Pd and in between the stenosis Ps by pulling the pressure guidewire back in position. Let us assume no significant branch is present, there are now two sets of relations 8 and 9 for each segment 40 and 41. Flow in both segments is the same while pressure difference of first segment is $\Delta p_{s1} = p_a - p_s$ and $\Delta P_{s2} =$ $(p_a-p_d)-\Delta p_{s1}$. Parameters $A_{s1}$ and $B_{s1}$ for first segment 40 and $A_{s2}$ and $B_{s2}$ for the second segment 41 are known. From there, we calculate mean microvascular resistance $R_M$.

Assuming no diffuse disease is present in the first segment 40, we can assume the stenting of one stenosis, let us assume stenosis 1, leads to the elimination of the pressure drop in this segment. The artery can therefore be modeled using the second set of parameters only. Removing stenosis 1 however leads to a new flow, given by $Q_{Post-PCI}=P_{d\,post-PCI}/R_M$. By inserting this relation into relation 9 leads to $$p_a^S - p_d^S = A_{S2}\left(\frac{p_d^s}{R_M}\right) + B_{S2}\left(\frac{p_d^s}{R_M}\right)^2, \qquad 26$$

which is easily resolved for $p_d^S$ by posing $p_a^S$. Post-PCI FFR is then $FFR=p_d^S/p_a^S$. It is understood this is one example and other segmentations can be used to also take into consideration diffuse diseases or other features as provided herein.

Other Models

Although the description herein is mostly based on the use of a second-order model, i.e., a model relating the pressure drop with the addition of a linear term and a second-order blood flow term such as relations 8 and 9, to characterize the artery pressure-flow relation, other models can be used. For instance, models where two or more pressure measurements and corresponding (and simultaneous) images are acquired while the flow is different such as during systole vs. diastole, or during resting vs. hyperemic conditions, can be used as well. The systole vs. diastole act as first and second blood flow conditions, and so do the resting vs. hyperemic conditions. By way of non-limiting examples, other models may include a third order term, or may comprise differential or integral terms, time-dependent terms, space-dependent terms, etc.

Co-Registration

Considering the embodiments above includes hemodynamic information that relates to specific regions of the artery, it would facilitate the visualization and assessment of the hemodynamic functions if they were integrated along with the angiogram in way similar to U.S. patent application US 2006/0052700 entitled "Pressure measurement system", incorporated herein by reference in its entirety.

Although the microvascular resistance is considered herein as purely resistive, it is also possible to assume the microvascular impedance contains a capacitance in addition to resistors (Morris et al., JACC Vol. 8, No. 9 2015), and calculate both the microvascular resistance and capacitance.

According to the embodiments of the invention, a computing system is required to advantageously compute the hemodynamic parameters listed above according to the relations also described above in a timely manner, since the values need to be computed in real time during intervention for rapid and critical decision-making. The computing system comprises a memory for storing instructions, notably those for computing the hemodynamic parameters. A processor in communication with the memory executes the instructions to perform the computations.

The computing system has ports of communication (which can be wired or wireless) for receiving pressure measurements from the pressure guidewire 2. The pressure guidewire 2 comprises a pressure sensor which transmits its signals through a communication means (electrical or preferably optical) through the pressure guidewire, to a receiver which processes the signal to feed it to the computing system, or directly to the computing system if it is adapted to receive such a signal from the pressure guidewire. The computing system thus receives pressure measurements as required by the embodiments described herein.

Image data taken by imaging instruments is also fed to the computing system simultaneously to the data from the pressure guidewire, such that pressure measurements are simultaneously complemented with real image data of local and personalized artery geometry.

Instead of using a non-invasive method as a replacement for the invasive methods, both invasive (pressure guidewire) and non-invasive (imaging) are used together as complements in order to calculate more accurate hemodynamic parameters. The computing system receives both data sources to compute in real-time the hemodynamic parameters and offer to the clinician a hemodynamic parameter value that is more representative of the real local conditions in the coronary artery being investigated, thus allowing better decision making in the cath lab as the hemodynamic parameters better reflect reality instead of assuming incorrect generalities regarding artery geometry.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method executable by a computing system comprising a processor in communication with an intravascular pressure measurement device and with a medical imaging instrument, the method comprising:

measuring, by the intravascular pressure measurement device, at least one pressure measurement in an artery using an intravascular pressure measurement device;

synchronously with measuring the al least one pressure measurement, taking, with a medical imaging instrument, at least one medical image of the artery, wherein each of the at least one pressure measurement has a corresponding synchronous medical image of the artery;

feeding both the at least one pressure measurement and the at least one medical image to the computing system:

calculating, by the processor, a flow from the al least one medical image;

calculating parameters representative of the artery itself and distinct from the flow, wherein each one of the parameters is a polynomial coefficient of a polynomial relationship between a pressure drop and a corresponding flow component, the parameters being calculated from at least two artery pressure drops, which are different, and corresponding flow components, each calculated from the at least one medical image;

based on the flow and the parameters representative of the artery, calculating a patient-specific hemodynamic parameter of microvascular resistance, at rest or stressed and over the whole heartbeat, during diastole or systole, or other time frames (Rm) and coronary flow reserve (CFR); and providing, by the computing system, the patient-specific hemodynamic parameter to a clinician for decision-making.

2. The method of claim 1, wherein the steps of measuring the at least one pressure measurement and taking the at least one medical image are performed in two conditions of blood flow, wherein calculating parameters of the artery comprises solving a second-degree equation of the parameters of the artery using the at least two artery pressure drops and corresponding flow components which are measured in the two conditions of blood flow.

3. The method of claim 2, wherein the two conditions of blood flow comprise a higher blood flow condition and a lower blood flow condition, the method further comprising administering an agent to cause higher blood flow condition prior to said steps of measuring the at least one pressure measurement and taking the at least one medical image under the higher blood flow condition.

4. The method of claim 3, wherein the higher blood flow condition is induced by injection of contrast agent or hyperemic agent to induce partial or full hyperemia.

5. The method of claim 3, further comprising producing a sound signal when inducing the higher blood flow condition for timing the step of measuring the at least one pressure measurement with the injection of a microvascular dilator agent.

6. The method of claim 3, further comprising introducing a radiation-absorbing contrast medium in the artery, wherein taking the at least one medical image of the artery further comprises:
measuring, in the at least one medical image, a diameter D of the artery which varies along a length x of the artery;
tracking a propagation of the radiation-absorbing contrast medium in the artery and measuring a time taken for a propagation between a first point L1 to a second point L2 in the artery,
wherein calculating the flow comprises dividing a volume V, $$V = \frac{(L_2 - L_1)}{4} \cdot \int_{L1}^{L2} \pi (D(x))^2 dx,$$

by the time taken for the propagation to calculate a mean blood flow in the artery.

7. The method of claim 6, wherein measuring, in the at least one medical image defining a plane, the diameter D of the artery which is perpendicular to the plane of the at least one medical image comprises using densitometry on the radiation-absorbing contrast medium to measure D as a function of x by applying Beer-Lamberts law on a measured intensity in a section of the artery.

8. The method of claim 3, further comprising inducing hyperemic condition using an intracoronary or intravenous injection of a hyperemic agent in the artery, and calculating the flow associated to the hyperemic condition using the parameters of the artery, wherein calculating the patient-specific hemodynamic parameter is based on a pressure drop and the calculated flow associated to the hyperemic condition.

9. The method of claim 2, wherein the steps of measuring the at least one pressure measurement and taking the at least one medical image are performed in a resting condition, first during a systole period which covers at least a portion of a systole, and second during a diastole period which covers at least a portion of the diastole, wherein calculating parameters of the artery comprises solving a second-degree equation of the parameters of the artery using the at least two artery pressure drops and corresponding flow components which are respectively measured and calculated in the systole period and in the diastole period.

10. The method of claim 1, further comprising identifying a presence of a stenosis in the artery and identifying a segment distal from the stenosis which is free of any stenosis, and taking a plurality of pressure measurements along said segment.

11. The method of claim 10, wherein identifying a presence of a stenosis comprises comparing one of the parameters of the artery with a predetermined threshold to identify a presence of a stenosis in the artery.

12. The method of claim 10, wherein identifying a presence of a stenosis comprises using the at least one medical image to identify a presence of a stenosis in the artery by determining a presence of a luminal obstruction above 50%.

13. The method of claim 10, wherein taking a plurality of pressure measurements along said segment is made by providing a tip of the intravascular pressure measurement device at a most distal location in said segment and pulling back the intravascular pressure measurement device.

14. The method of claim 10, further comprising calculating a geometry-based flow using the plurality of pressure measurements along said segment and numerically solving Navier-Stokes equations, and using the geometry-based flow to apply corrections to the parameters of the artery and to the step of calculating a flow from the at least one medical image, thereby applying a correction to the patient-specific hemodynamic parameter to account for the presence of the stenosis.

15. The method of claim 1, wherein measuring the at least one pressure measurement and taking at least one medical image are synchronous by simultaneously acquiring the at least one pressure measurement and the at least one medical image in real time, or by time stamping the at least one pressure measurement and the at least one medical image.

* * * * *